US007901555B2

(12) United States Patent
Jiang et al.

(10) Patent No.: US 7,901,555 B2
(45) Date of Patent: Mar. 8, 2011

(54) ELECTRO-CHEMICAL SENSOR

(75) Inventors: Li Jiang, Ridgefield, CT (US); Timothy Gareth John Jones, Cottenham (GB); Richard Compton, Oxford (GB); Nathan Lawrence, St Neots (GB); Gregory George Wildgoose, Oxford (GB); Malingappagari Pandurangappa, Bangalore (IN); Oliver Clinton Mullins, Ridgefield, CT (US); Andrew Meredith, Cambridge (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 596 days.

(21) Appl. No.: 10/585,263

(22) PCT Filed: Dec. 22, 2004

(86) PCT No.: PCT/GB2004/005397
§ 371 (c)(1),
(2), (4) Date: May 17, 2007

(87) PCT Pub. No.: WO2005/066618
PCT Pub. Date: Jul. 21, 2005

(65) Prior Publication Data
US 2007/0272552 A1    Nov. 29, 2007

(30) Foreign Application Priority Data
Jan. 8, 2004  (GB) .................................. 0400325.7

(51) Int. Cl.
*G01N 27/333* (2006.01)
*E21B 47/00* (2006.01)
*E21B 49/00* (2006.01)

(52) U.S. Cl. ....... 204/416; 204/433; 204/418; 205/787.5

(58) Field of Classification Search .......... 205/775–791, 205/792; 204/400–434
See application file for complete search history.

(56) References Cited

U.S. PATENT DOCUMENTS

| 3,780,575 | A |   | 12/1973 | Urbanosky |
| 3,859,851 | A |   | 1/1975  | Urbanosky |
| 4,994,671 | A |   | 2/1991  | Safinya et al. |
| 5,005,406 | A |   | 4/1991  | Jasinski et al. |
| 5,223,117 | A | * | 6/1993  | Wrighton et al. ............. 204/415 |
| 5,351,532 | A |   | 10/1994 | Hager |
| 5,445,228 | A |   | 8/1995  | Rathmell et al. |
| 5,489,371 | A |   | 2/1996  | Joseph et al. |
| 5,517,024 | A |   | 5/1996  | Mullins et al. |

(Continued)

FOREIGN PATENT DOCUMENTS

DE    102 51 183 A    7/2003

(Continued)

OTHER PUBLICATIONS

Wang et al. (Carbon nanotube screen-printed electrochemical sensors, Analyst, 2003, 129, 1-2).*

(Continued)

*Primary Examiner* — Alexa D Neckel
*Assistant Examiner* — Jennifer Dieterle
(74) *Attorney, Agent, or Firm* — Vincent Loccisano; James McAleenan; Brigid Laffey

(57) ABSTRACT

An electro-chemical sensor is described having two molecular redox systems sensitive to the same species and having an detector to detect relative shifts in the voltammograms of the two redox systems.

12 Claims, 13 Drawing Sheets

U.S. PATENT DOCUMENTS

| | | | |
|---|---|---|---|
| 5,518,590 | A | 5/1996 | Fang |
| 5,676,820 | A | 10/1997 | Wang et al. |
| 5,736,650 | A | 4/1998 | Hiron et al. |
| 5,829,520 | A | 11/1998 | Johnson |
| 6,023,340 | A | 2/2000 | Wu et al. |
| 6,262,941 | B1 | 7/2001 | Naville |
| 2002/0090632 | A1* | 7/2002 | Buck et al. .................... 435/6 |
| 2003/0206026 | A1* | 11/2003 | Diakonov et al. ............ 324/723 |
| 2008/0035481 | A1 | 2/2008 | McCormack et al. |
| 2009/0178921 | A1 | 7/2009 | Lawrence et al. |

FOREIGN PATENT DOCUMENTS

| | | |
|---|---|---|
| GB | 2 362 469 A | 11/2001 |
| WO | 99/00575 A3 | 1/1999 |

OTHER PUBLICATIONS

Kuo et al. (Electrochemical modification of boron-doped chemical vapor deposited diamond surfaces with covalently bonded monolayers, Electrochemical and Solid-State Letters, 2 (6), 1999, 288-290).*

Pandurangappa et al. (Physical adsorption of N,N'-diphenyl-p-phenylenediamine onto carbon particles: Application to the detection of sulfide, Analyst, 2003, 128, 473-479).*

Wildgoose et al. (Anthraquinone-derivatised carbon powder: reagentless voltammetric pH electrodes, Talanta, 60, 2003, pp. 887-893).*

Casimari et al. (Co-immobilized L-lactate oxidase and L-lactate dehydrogenase on a film mounted on oxygen electrode for highly sensitive L-lactate determination, Biosensors & Bioelectronics, 1995, vol. 11, No. 8, pp. 783-789).*

Casimiri et al., Co-immobilized L-lactate oxidase and L-lactate dehydrogenase on a film mounted on oxygen electrode for highly sensitive L-lactate determination, vol. 11, No. 8, 1996, pp. 783-789.*

Carter et al 'Voltammetric studies of the interaction of tris (1,10-phenanthroline)-cobalt (III) with DNA' Journal of the American Chemical Society, 1987, 109, p. 7528-7530.

Downward 'Electrochemically assisted covalent modification of carbon electrodes' Electroanalysis, 2000, 12, p. 1085-1096.

Galster 'pH measurement: fundamentals, methods, applications, instrumentation' VCH Weinheim, 1991, p. 20-28.

Hickman et al 'Molecular self-assembly of two-terminal voltammetric microsensors with internal references' Science, 1991, 252, 688-691.

Lawrence et al 'Voltammetric characterization of a N,N'-Diphenyl-p-phenylenediamine-loaded screen-printed electrode: a disposable sensor for hydrogen sulfide' Analytical Chemistry, 2003, 75, p. 2054-2059.

Scholz et al 'Voltammetry of solid microparticles immobilized on electrode surfaces' Electroanalytical Chemistry; A Series of Advances, Marcel Dekker Inc. New York, 1998, 20, p. 1-86, ed. Bard et al.

Solodov et al 'Distribution and geochemistry of contaminated subsurface waters in fissured volcanogenic bed rocks of the Lake Karachai area, Chelyabinsk, Southern Urals' Lawrence Berkeley Laboratory Report 36780/UC-603, 1994, USA.

Wildgoose et al 'Anthraquinone-derivatised carbon powder: reagentless voltammetric pH electrodes' Elsevier, Talanta, 2003, 60, p. 887-893.

Woodhawan et al. "Voltammetric characteristics of graphite electrodes modified with microdroplets of n-butylferrocence", Journal of Electroanalytical Chemistry, 2002, vol. 533, 71-84.

* cited by examiner

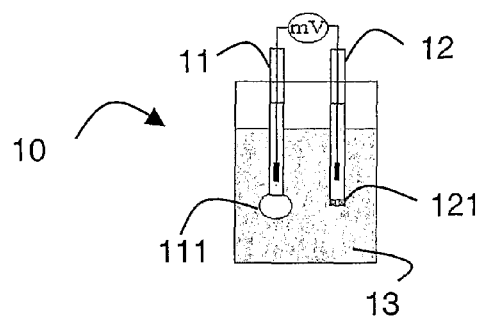
FIG. 1
(Prior Art)
FIG. 2A
(Prior Art)
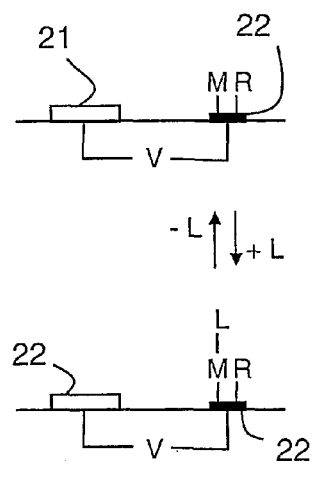
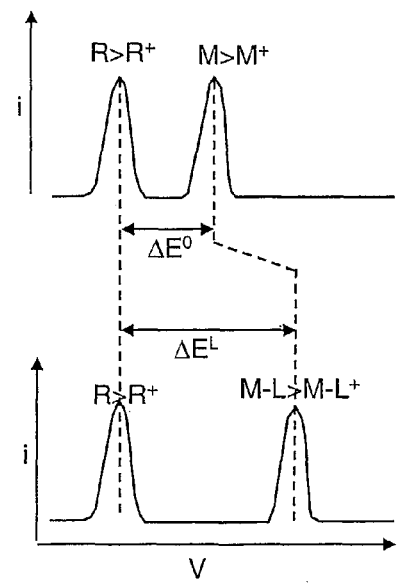
FIG. 2B
(Prior Art)
FIG. 2C
(Prior Art)

FIG. 4C
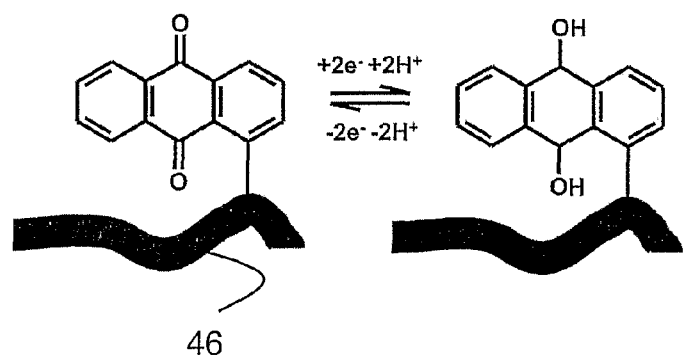
46
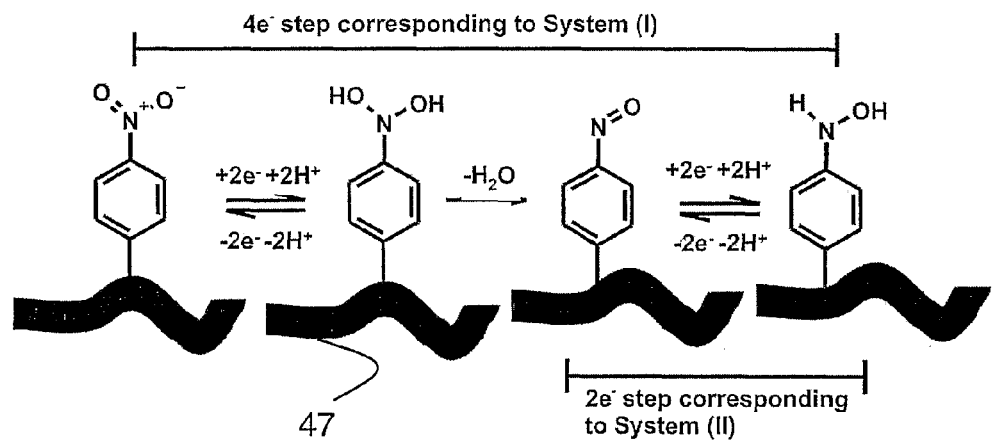
47
FIG. 4D

ELECTRO-CHEMICAL SENSOR

The invention relates to a chemical sensor tool for use in downhole and methods for analyzing of fluids produced from subterranean formations. More specifically it relates to a electro-chemical sensor for downhole pH and ion content analysis of effluents produced from subterranean formation.

CROSS-REFERENCE TO RELATED APPLICATIONS

This application claims the benefits of priority from:
i) Application Number 0400325.7, entitled "ELECTRO-CHEMICAL SENSOR," filed in the United Kingdom on Jan. 8, 2004; and
ii) Application Number PCT/GB2004/005397, entitled "ELECTRO-CHEMICAL SENSOR," filed under the PCT on Dec. 22, 2004;
All of which are commonly assigned to assignee of the present invention and hereby incorporated by reference in their entirety.

BACKGROUND OF THE INVENTION

Analyzing samples representative of downhole fluids is an important aspect of determining the quality and economic value of a hydrocarbon formation.

Present day operations obtain an analysis of downhole fluids usually through wireline logging using a formation tester such as the MDT™ tool of Schlumberger Oilfield Services. However, more recently, it was suggested to analyze downhole fluids either through sensors permanently or quasi-permanently installed in a wellbore or through sensor mounted on the drillstring. The latter method, if successfully implemented, has the advantage of obtaining data while drilling, whereas the former installation could be part of a control system for wellbores and hydrocarbon production therefrom.

To obtain an estimate of the composition of downhole fluids, the MDT tools uses an optical probe to estimate the amount of hydrocarbons in the samples collected from the formation. Other sensors use resistivity measurements to discern various components of the formations fluids.

Particularly, knowledge of downhole formation (produced) water chemistry is needed to save costs and increase production at all stages of oil and gas exploration and production. Knowledge of particularly the water chemistry is important for a number of key processes of the hydrocarbon production, including:
  Prediction and assessment of mineral scale and corrosion;
  Strategy for oil/water separation and water re-injection;
  Understanding of reservoir compartmentalization/flow units;
  Characterization of water break-through;
  Derivation of the water cut $R_w$; and
  Evaluation of downhole the $H_2S$ partition the oil and or water (if used for $H_2S$ measurements).

Some chemical species dissolved in water (like, for example, $Cl^-$ and $Na^+$) do not change their concentration when removed to the surface either as a part of a flow through a well, or as a sample taken downhole. Consequently information about their quantities may be obtained from downhole samples and in some cases surface samples of a flow. However, the state of chemical species, such as $H^+$ (pH=−log [concentration of $H^+$]), $CO_2$, or $H_2S$ may change significantly while tripping to the surface. The change occurs mainly due to a difference in temperature and pressure between downhole and surface environment. In case of sampling, this change may also happen due to degassing of a sample (seal failure), mineral precipitation in a sampling bottle, and (especially in case of $H_2S$)— a chemical reaction with the sampling chamber. It should be stressed that pH, $H_2S$, or $CO_2$ are among the most critical parameters for corrosion and scale assessment. Consequently it is of considerable importance to have their downhole values precisely known.

The concentration of protons or its logarithm pH can be regarded as the most critical parameter in water chemistry. It determines the rate of many important chemical reactions as well as the solubility of chemical compounds in water, and (by extension) in hydrocarbon.

Hence, there is and will continue to be a demand for downhole chemical measurements. However, no downhole chemical measurements actually performed in an oil and gas producing well have been reported so far, though many different methods and tools have been proposed in the relevant literature.

General downhole measurement tools for oilfield applications are known as such. Examples of such tools are found in the U.S. Pat. Nos. 6,023,340; 5,517,024; and 5,351,532 or in the International Patent Application WO 99/00575. An example of a probe for potentiometric measurements of ground water reservoirs is further published as: Solodov, I. N., Velichkin, V. I., Zotov, A. V. et al. "Distribution and Geochemistry of Contaminated Subsurface Waters in Fissured Volcanogenic Bed Rocks of the Lake Karachai Area, Chelyabinsk, Southern Urals" in: Lawrence Berkeley Laboratory Report 36780/UC-603(1994b), RAC-6, Ca, USA.

The known state of the art in the field of high temperature potentiometric measurements and tool is described for example in the published UK patent application GB-2362469 A.

A number of chemical analysis tools are known from chemical laboratory practice. Such known analysis tools include for example the various types of chromatography, electrochemical and spectral analysis. Particularly, the potentiometric method has been widely used for the measurements of water composition (pH, Eh, $H_2S$, $CO_2$, $Na^+$, $Cl^-$ etc.) both in the laboratory and in the field of ground water quality control. U.S. Pat. No. 5,223,117 discloses a two-terminal voltammetric microsensor having an internal reference using molecular self-assembling to form a system in which the reference electrode and the indicator electrode are both on the sensor electrode. The reference molecule is described as a redox system that is pH-insensitive, while the indicator molecule is formed by a hydro-quinone based redox system having a potential that shifts with the pH. Both, reference molecule and indicator molecule layers are prepared by self-assembly on gold (Au) microelectrodes. In the known microsensor, a pH reading is derived from peak readings of the voltagrams.

The laboratory systems, however, are often not suitable for wellbore application with demands for ruggedness, stability and low maintenance and energy consumption being rarely met.

It is therefore an object of the present invention to provide apparatus and methods to perform electrochemical measurements in hydrocarbon wells during drilling and production. More specifically, it is an object of the present invention to provide robust sensors for molecularly selective electrochemical measurements, in particular pH measurements.

SUMMARY OF THE INVENTION

The invention achieves its objects by providing an electrochemical sensor having a measuring electrode with at least two receptors sensitive to the same species.

In a preferred variant of the invention the sensors are a redox system, based for example on anthraquinone chemistry.

The substrate onto which the redox system is mounted is preferable based on carbon in one of its elementary forms such as graphite, carbon powder, diamond. In a variant of the invention the substrate may be derivatised nanotubes, including multi-walled nanotubes An electrochemical technique using a method or sensor in accordance with the present invention can be applied for example as part of a production logging tool or an open hole formation tester tool (such as the Modular Dynamic Tester, MDT™). In the latter case, the technique can provide a downhole real-time water sample validation or downhole pH measurement which in turn can be used for predicting mineral scale and corrosion assessment.

These and other features of the invention, preferred embodiments and variants thereof, possible applications and advantages will become appreciated and understood by those skilled in the art from the following detailed description and drawings.

BRIEF DESCRIPTION OF DRAWINGS

FIG. 1 shows a schematic diagram of the main elements of a known voltametric sensor;

FIGS. 2A-C show schematic diagrams of the main elements of a known electro-chemical microsensor and its operation;

FIG. 4C illustrates the redox reaction of a measuring electrode in accordance with another example of the invention using multi-walled carbon nanotube;

FIG. 4D illustrates the redox reaction of a measuring electrode with internal reference electrode in accordance with another example of the invention using multi-walled carbon nanotube;

DETAILED DESCRIPTION OF THE INVENTION

Figure 3:
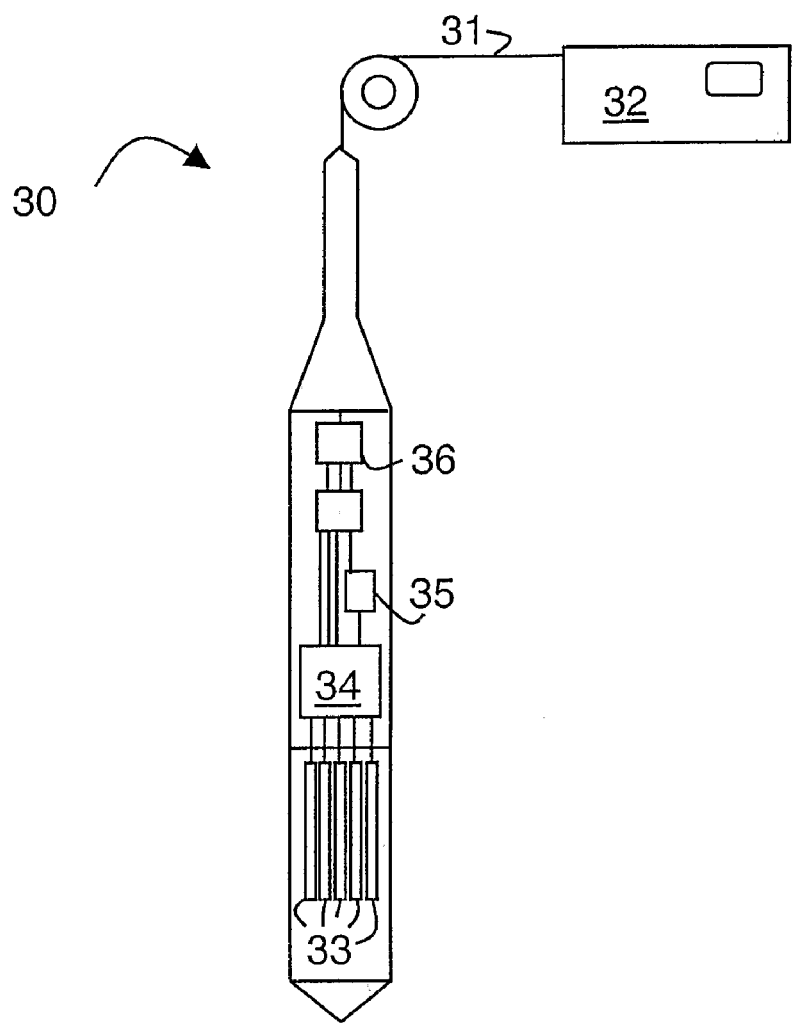
FIG. 3 shows a schematic diagram of a known downhole probe using potentiometric sensors.

The theory of voltammetry and its application to surface water measurements at ambient temperatures are both well developed. The method is based on the measurement of the electromotive force (e.m.f.) or potential E in a potentiometric cell which includes measuring and reference electrodes (half-cells).

FIG. 1 shows the general components of a known voltammetric cell 10. A measuring electrode 11 is inserted into a solution 13. This electrode consists of an internal half element (for example, Ag wire covered by an AgCl salt) in a solution of a fixed pH (for example, 0.1M HCl in some pH electrodes), and an ion-selective membrane 111 (like glass $H^+$ selective membrane in pH glass electrode). The reference electrode 12 also contains an internal half-element (typically the same AgCl; Ag) inserted in a concentrated KCl (for example 3M) solution/gel saturated with $Ag^+$, which diffuses (or flows) through the reference (liquid) junction 121.

The ion-selective electrode 11 measures the potential that arises because of the difference in activity or concentration of a corresponding ion ($H^+$ in case of pH) in the internal solution and in the measured solution. This potential is measured against the reference potential on the reference electrode 12, which is fixed because of a constant composition of a reference solution/gel. The electrodes may be separated (separate half cells), or combined into one ("combination electrode").

The measured e.m.f. is an overall function of the temperature and the activity of an ith ion, to which the measuring electrode is selective:

$$E=E^0+(k*T)*\log(a_i),  \quad [1]$$

where E is the measured electromotive force (e.m.f.) of the cell (all potentials are in V), $a_i$ corresponds to the activity of the ith ion and is proportional to its concentration. $E^0$ is the standard potential (at temperature T) corresponding to the E value in a solution with the activity of ith ion equal to one. The term in parenthesis is the so-called Nernstian slope in a plot of E as a function of $\log(a_i)$. This slope (or the constant "k") together with the cell (electrode) constant ($E^0$) is experimentally determined via a calibration procedure using standard solutions with known activities of ith ion. For good quality undamaged electrodes this slope should be very close to the theoretical one, equal to (R*T/F*z), where F is the Faraday constant (23061 cal/mole), R is the gas constant (1.9872 cal/mole K), $z_i$ is the charge of ith ion.

The Nernst equation [1] can be rewritten for pH sensors, i.e. log a($H^+$) as $$E_{0.5}=K-(2.303 \text{ RTm/nF})\text{pH} \quad [2]$$

where $E_{0.5}$ is the half-wave potential of the redox system involved, K is an arbitrary constant, R is the ideal gas constant, m is the number of protons and n is the number of electrons transferred in the redox reaction.

The microsensor of U.S. Pat. No. 5,223,117 is illustrated in FIG. 2. FIG. 2A. shows a schematic electrochemical sensor with a counter electrode 21 and a relatively much smaller (by a factor of 1000) Au substrate 22 that carries two molecular species M and R. The R species forms an inert reference electrode, and species M is an indicator electrode with specific receptors or sensitivity for a third species L. The schematic linear sweep voltammogram in the upper half of FIG. 2C shows the difference in the current peaks for the oxidization in the normal state. When the third species L binds to M (FIG. 2B), this difference increases as illustrated by the shift of peaks in the lower half of FIG. 2C, thus providing a measure for the concentration of L in the solution surrounding the sensor. In the context of the present invention, it is important to note that the R is specifically selected to be insensitive to the species L, e.g. pH.

In FIG. 3, there are schematically illustrated elements of a known downhole analyzing tool 30 as used by Solodov et al (see background). The body of the tool 30 is connected to the surface via a cable 31 that transmits power and signals. A computer console 32 controls the tool, monitors its activity and records measurements. The tool 30 includes a sensor head with at number of selective electro-chemical probes 33 each sensitive to a different molecular species. Also housed in the body of the tool are further actuation parts 34 that operate the head, a test system 35 and transceivers 36 to convert measurements into a data stream and to communicate such data stream to the surface. The electrodes are located at the bottom part of the probe and include those for pH, Eh (or ORP), $Ca^{2+}$ (pCa), $Na^+$ (pNa), $S^{2-}$ (pS), $NH_4^+$ (pNH$_4$), and reference electrode (RE). $H_2S$ partial pressure may be calculated from pH and pS readings.

In the following aspects and elements of the present invention are described in detail.

The present invention introduces a new molecular system in which the redox features of two molecules are combined, thus leading to a considerably higher accuracy and, in turn, downhole deployability.

In a preferred embodiment for a pH sensitive sensor an anthraquinone is homogenously derivatised onto carbon particles (AQC)

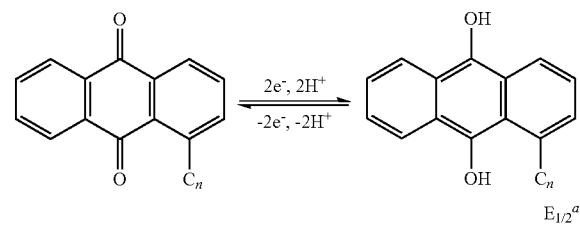

The AQC system is derived using 2 g of carbon powder (1.5 μm in mean diameter) mixed with a 10 cm$^3$ solution containing 5 mM Fast Red AL Salt (Anthraquinone-1-diazonium chloride) to which 50 mM hypophosphorous acid (50%) is added. The reaction is allowed to stand with occasional stirring at 5° C. for 30 minutes, after which it is filtered by water suction. Excess acid is removed by washing with distilled water and with the powder being finally washed with acetonitrile to remove any unreacted diazonium salt in the mixture. It is then air dried by placing inside a fume hood for a period of 12 hours and finally stored in an airtight container.

In a similar manner, phenanthrenequinone (PAQ)

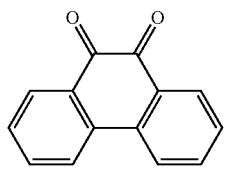

Is prepared as a second molecular species to undergo a redox reaction

Alternatively, N,N'-diphenyl-p-phenylenediamine (DPPD) spiked onto carbon particles undergoes a redox process as shown below:

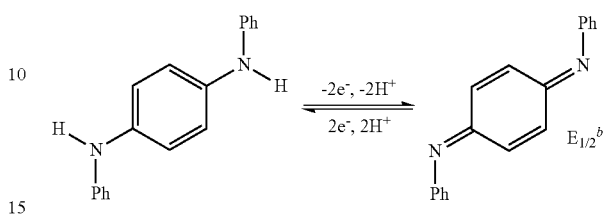

The bonding of DPPD onto carbon is achieved by mixing 4 g of carbon powder with 25 mL of 0.1M HCl+0.1M KCl and 20 mM DPPD solution in acetone. The reaction mixture is stirred continuously for 2 hours in a beaker and then filtered after which it was washed with distilled water to remove excess acid and chloride. It is then air dried by placing inside a fume hood for 12 hours and finally stored in an airtight container.

In a static environment where the sensor surface is not exposed to a flow, it is possible to immobilize water insoluble DPPD crystals directly onto the electrode surface. However in the wellbore environment it is preferred to link the sensitive molecules via a chemical bond to such surface.

The derivatised carbon powders are abrasively immobilised onto a basal plane pyrolytic graphite (BPPG) electrode prior to voltammetric characterisation following a procedure described by Scholz, F. and Meyer, B., "Voltammetry of Solid Microparticles Immobilised on Electrode Surfaces in Electroanalytical Chemistry" ed. A. J. Bard, and I. Rubenstein, Marcel Dekker, New York, 1998, 20, 1. Initially the electrode is polished with glass polish paper (H00/240) and then with silicon carbide paper (P1000C) for smoothness. The derivatised carbons are first mixed and then immobilised onto the BPPG by gently rubbing the electrode surface on a fine qualitative filter paper containing the functionalised carbon particles.

Figure 4A:
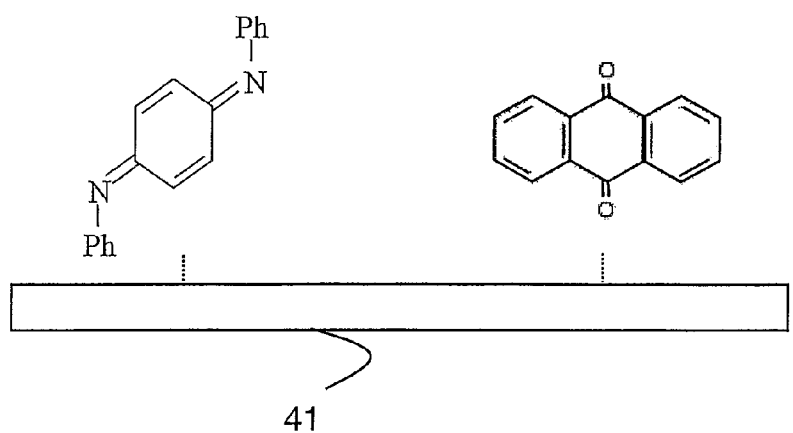
FIG. 4A illustrates the surface structure of a measuring electrode in accordance with an example of the invention.

The resulting modified electrode surface is schematically illustrated by FIG. 4A showing an electrode 41 with bonded DPPD and AQC.

It is further advantageous too add an internal pH reference involving a pH independent redox couple to increase the stability of any voltammetric reading, hence circumventing uncertainties caused by fouling of the external reference electrode. In the configuration, the sensor includes two reference electrodes.

A suitable reference molecule is, for example, $K_5MO(CN)_8$ or polyvenylferrocene (PVF) which both have a stable redox potential ($K_5Mo(CN)_8$ at around 521 mV) that is sufficiently separated from expected shifting of redox signals of the two indicator species over the pH range of interest. As shown in Table 1 that both the oxidation and reduction potentials of $K_5Mo(CN)_8$ are fairly constant across the entire pH range of interest.

TABLE 1

| pH | $AQ_{OX}$ | $AQ_{RED}$ | $DPPD_{OX}$ | $DPPD_{RED}$ | Mo—$_{OX}$ | Mo—$_{RED}$ |
|---|---|---|---|---|---|---|
| 4.6 | −0.440 | −0.448 | 0.202 | 0.224 | 0.524 | 0.524 |
| 6.8 | −0.576 | −0.580 | 0.094 | 0.082 | 0.528 | 0.522 |
| 9.2 | −0.710 | −0.674 | −0.204 | −0.372 | 0.512 | 0.508 |

The Mo-based reference species can be retained in the solid substrate via ionic interactions with co-existing cationic polymer, such as poly (vinyl pyridine), that was spiked into the solid phase. Other pH independent species, such as ferrocyanide are less suitable as the redox peaks are obscured by the signals of the measuring redox system.

Figure 4B:
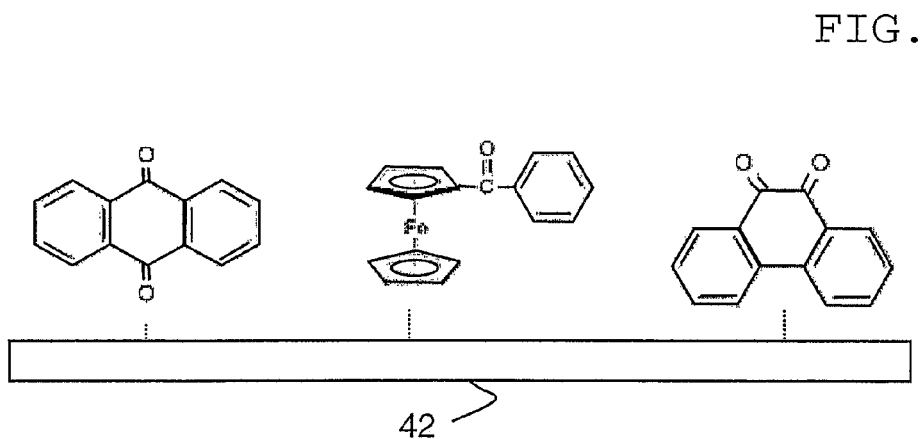
FIG. 4B illustrates the surface structure of a measuring electrode with internal reference electrode in accordance with another example of the invention.

In FIG. 4B the electrode 42 carries bonded molecules AQC and PAQ together with PVF as an internal reference molecule.

The most common forms of conducting carbon used in electrode manufacture are glassy carbon, carbon fibres, carbon black, various forms of graphite, carbon paste and carbon epoxy. One further form of carbon, which has seen a large expansion in its use in the field of electrochemistry since its discovery in 1991 is the carbon nanotube (CNT). The structure of CNTs approximates to rolled-up sheets of graphite and can be formed as either single or multi-walled tubes. Single-walled carbon nanotubes (SWCNTs) constitute a single, hollow graphite tube. Multi-walled carbon nanotubes (MWCNTs) on the other hand consist of several concentric tubes fitted one inside the other.

The above activation methods for binding a redox active species to graphite or carbon surfaces can be extended via the chemical reduction of aryldiazonium salts with hypophosphorous acid, to include the covalent derivatisation of MWCNTs by anthraquinone-1-diazonium chloride and 4-nitrobenzenediazonium tetrafluoroborate. This results in the synthesis of 1-anthraquinonyl-MWCNTs (AQ-MWCNTs) and 4-nitrophenyl-MWCNTs (NB-MWCNTs) as shown in FIGS. 4C and 4D, respectively. The respective substrates 46 and 47 are multi-walled carbon nanotubes.

The preparation process of the derivatised MWCNT involves the following steps: first 50 mg of MWCNTs are stirred into 10 cm$^3$ of a 5 mM solution of either Fast Red AL (anthraquinone-1-diazonium chloride) or Fast Red GG (4-nitrobenzenediazonium tetrafluoroborate), to which 50 cm$^3$ of hypophosphorous acid ($H_3PO_2$, 50% w/w in water) is added. Next the solution is allowed to stand at 5° C. for 30 minutes with gentle stirring. After which, the solution is filtered by water suction in order to remove any unreacted species from the MWCNT surface. Further washing with deionised water is carried out to remove any excess acid and finally with acetonitrile to remove any unreacted diazonium salt from the mixture. The derivatised MWCNTs arethen air-dried by placing them inside a fume hood for a period of 12 hours after which they are stored in an airtight container prior to use. Untreated multi-walled nonotubes can be purchased from commercial verndors, for example from Nano-Lab Inc of Brighton, Mass., USA in 95% purity with a diameter of 30+/−15 nm and a length of 5-20 μm.

The reduction of diazonium salts using hypophosphorous acid as demonstrated is a versatile technique for the derivatisation of bulk graphite powder and MWCNTs. This has the advantage over previous methods involving the direct electrochemical reduction of aryldiazonium salts onto the electrode surface, as our chemically activated method allows the possibility for inexpensive mass production of chemically derivatised nanotubes for a variety of applications. Furthermore the derivatisation of MWCNTs proffers the possibility of sensor miniaturisation down to the nano-scale.

Figure 4E:
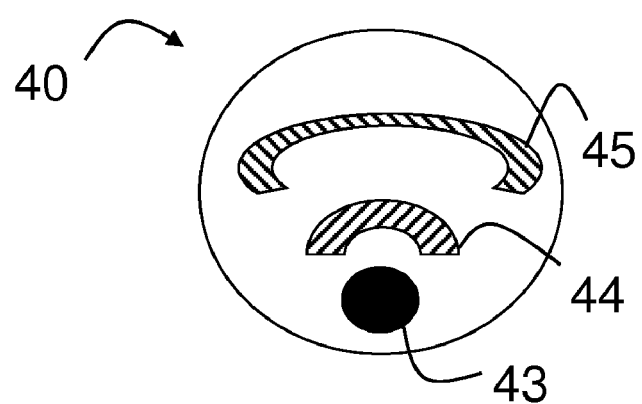
FIG. 4E illustrates the geometrical surface layout of the electrode of FIG. 4B.

In FIG. 4E there is shown a possible geometric configuration or layout for the sensor surface 40 which is exposed to the wellbore fluid. The surface includes a working electrode 43 as described in FIG. 4A or 4B, together with the (external) reference electrode 44 and a counter electrode 45.

Figure 5:
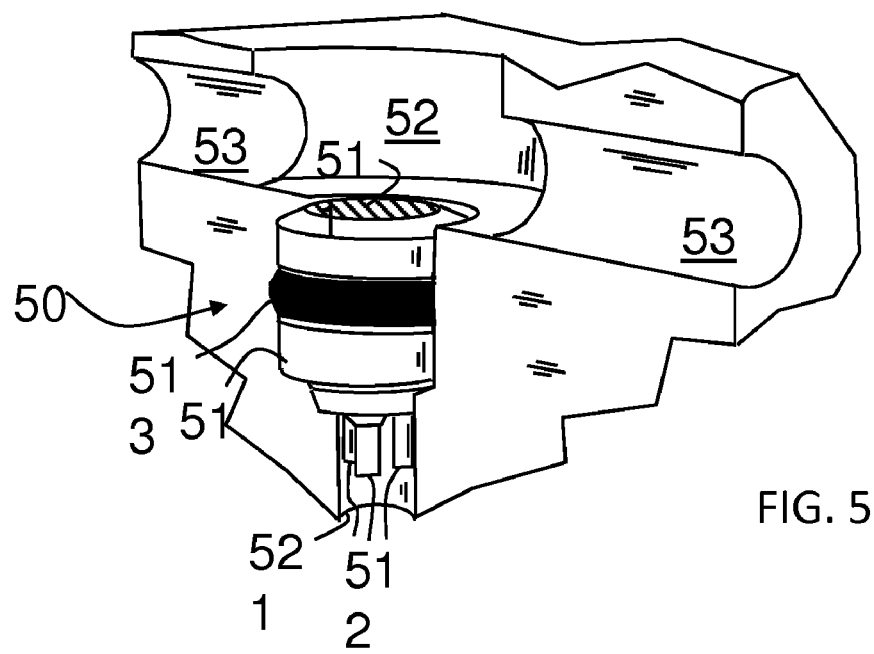
FIG. 5 is a perspective view, partially cut-away, of a sensor in accordance with an example of the present invention in a downhole tool.

A schematic of a microsensor 50 incorporating a modified surface prepared in accordance with the procedure described above is shown in FIG. 5. The body 51 of the sensor is fixed into the end section of an opening 52. The body carries the electrode surface 511 and contacts 512 that provide connection points to voltage supply and measurement through a small channel 521 at the bottom of the opening 52. A sealing ring 513 protects the contact points and electronics from the wellbore fluid that passes under operation conditions through the sample channel 53.

It is an advantage of the new sensor to include two measuring or indicator electrodes or molecules measuring two e.m.f or potentials with reference to the same reference electrode and being sensitive to the same species or molecule in the environment. As a result the sensitivity towards a shift in the concentration of the species increases. Using the above example of AQC and DPPA and the pH (or $H^+$ concentration, the Nernst equation applicable to the new sensor is the sum of the equations describing the individual measuring electrodes. Thus, combining the half wave potential $E_{0.5}$ (AQC) for anthraquinone $$E_{0.5}(AQC)=K(AQC)-(2.303\ RTm/nF)pH \qquad [3]$$

with the half wave potential $E_{0.5}$(DPPD) for N,N'-diphenyl-p-phenylenediamine $$E_{0.5}(DPPD)=K(DPPD)-(2.303\ RTm/nF)pH \qquad [4]$$

yields the half wave potential $E_{0.5}$(S) for the combined system:

$$E_{0.5}(S)=E_{0.5}(AQC)+E_{0.5}(DPPD)=(K(AQC)+K(DPPD))-2*(2.303\ RTm/nF)pH=K(S)-2*(2.303\ RTm/nF)pH \qquad [5]$$

Where K(S) is the sum of the two constants K(AQC) and K(DPPD). As the shift of the potential with a change in pH depends on the second term, the (theoretical) sensitivity of the sensor has doubled.

The use of a further (third) redox system sensitive to the same species would in principle increase the sensitivity further. As the method detects shifts in the peak location of the voltammogram, however, more efforts are anticipated to be required to resolve overlapping peaks in such a three-molecule system.

Figure 6:
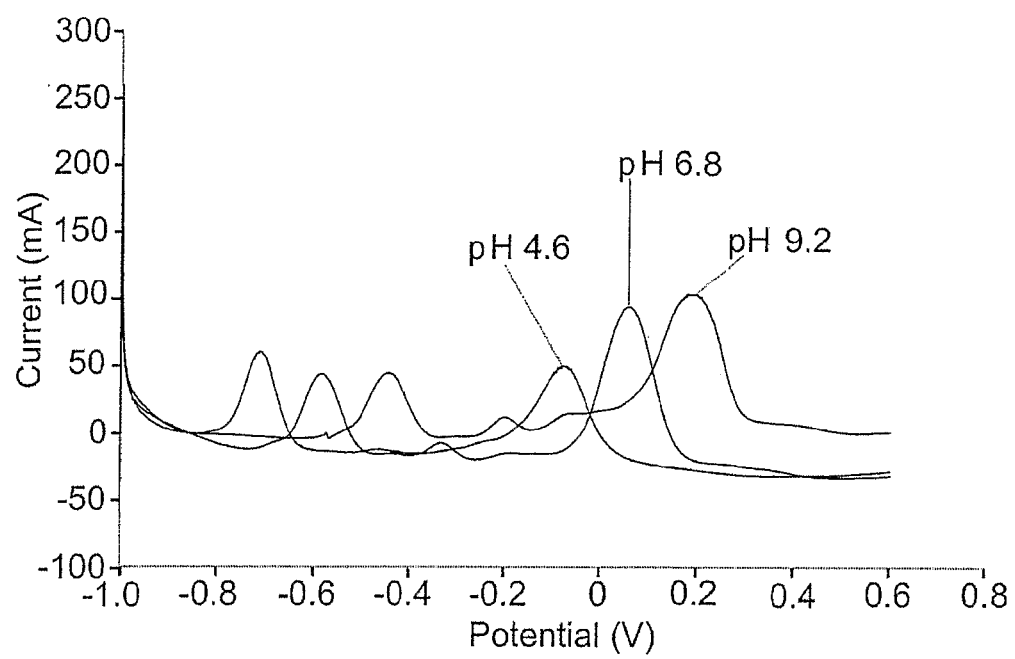
FIG. 6 shows voltammograms recorded from an electro-chemical microsensor in accordance with the present invention at three different pH values.

FIG. 6 shows results in a range of pH solutions (pH 4.6, 0.1M acetic acid+0.1M sodium acetate buffer; pH 6.8, 0.025M disodium hydrogen phosphate+0.025M potassium dihydrogen phosphate buffer; pH 9.2, 0.05M disodium tetraborate buffer). The figure presents the corresponding square wave voltammograms when the starting potential was sufficiently negative to have both DPPD and AQ in their reduced forms.

Figure 7A:
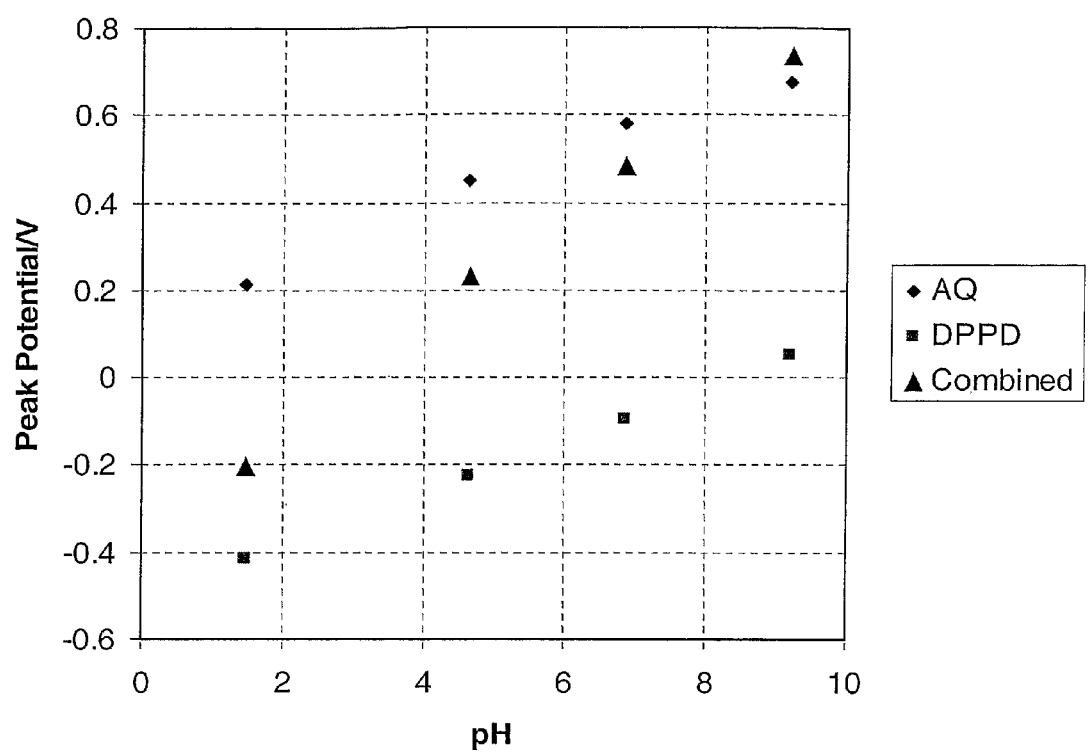
FIG. 7A illustrates the shift of the peak potential for anthraquinone, diphenyl-p-phenylenediamine and a combination of the two redox systems.

FIG. 7A depicts the relationship between the redox potential and pH for both the DPPD (■) and AQ (♦). The plot reveals a linear response from pH 4 to 9 with a corresponding gradient of ca 59 mV/pH unit (at 25° C.) which is consistent with an n electron, m proton transfer where n and m are likely to be equal to two. By combining the two individual curves in a manner as described in equation [5], a new function (▲) is derived with a superior sensitivity for the species to be detected.

For the two activated MWCNT species described above, the peak potential using cyclic voltammetry (CV) is found to be pH-dependant. This voltammetric behaviour is consistent with previous studies of carbon powder covalently modified with 1-anthraquinonyl groups and can be attributed to the two-electron, two-proton reduction/oxidation of the 1-anthraquinonyl moiety to the corresponding hydroquinone species.

When NB-MWCNTs is studied a more complicated voltammetric pattern can be observed. Upon first scanning in a reductive fashion a large, electrochemically irreversible peak is observed (labelled as system I), the exact peak potential of which depends on the pH studied. When the scan direction is reversed and swept in an oxidative fashion a new peak at more positive potentials than the irreversible peak is observed, which upon repeat cycling was found to behave in an electrochemically reversible fashion as the corresponding reduction wave was observed. This system is labelled as system II. Again the exact peak potential of system II is found to vary with the pH studied. This behaviour is consistent with the reduction mechanism, of the nitro moiety in aqueous media as exemplified by nitrobenzene in FIG. 4D. It is worth noting that all subsequent characterisation procedures for NB-MWCNTs are carried out on system II, which corresponds to the reversible arylnitroso/arylhydroxylamine couple, after several initial scans are performed to form this redox couple.

When investigating the effect of pH of AQ-MWCNTs and NB-MWCNTs over the range pH 1.0 to pH 12.0 using CV and square wave voltammetry (SWV) at room temperature as well as the behaviour of AQ-MWCNTs at elevated temperatures up to 70° C. SWV was used because it provides us with a sharp, well-defined peak in a single sweep. As concomitant proton loss/gain occurs on oxidation/reduction of AQ-MWCNTs or NB-MWCNTs (see FIGS. 4C and 4D respectively) the peak potential depends on the local proton concentration, i.e. pH, as described by the Nernst equation [6]:

$$E_{peak} = E_{formal}^{0} - \frac{2.3RTm}{nF} \text{pH} \quad [6]$$

where m and n, the number of protons and electrons transferred respectively, are both likely to be equal to two in the case of AQ-MWCNTs and the arylnitroso/arylhydroxylamine couple in the case of NB-MWCNTs. The formulation [6] of the Nernst equation is equivalent to those of equations [1] and [2].

Figure 7B:
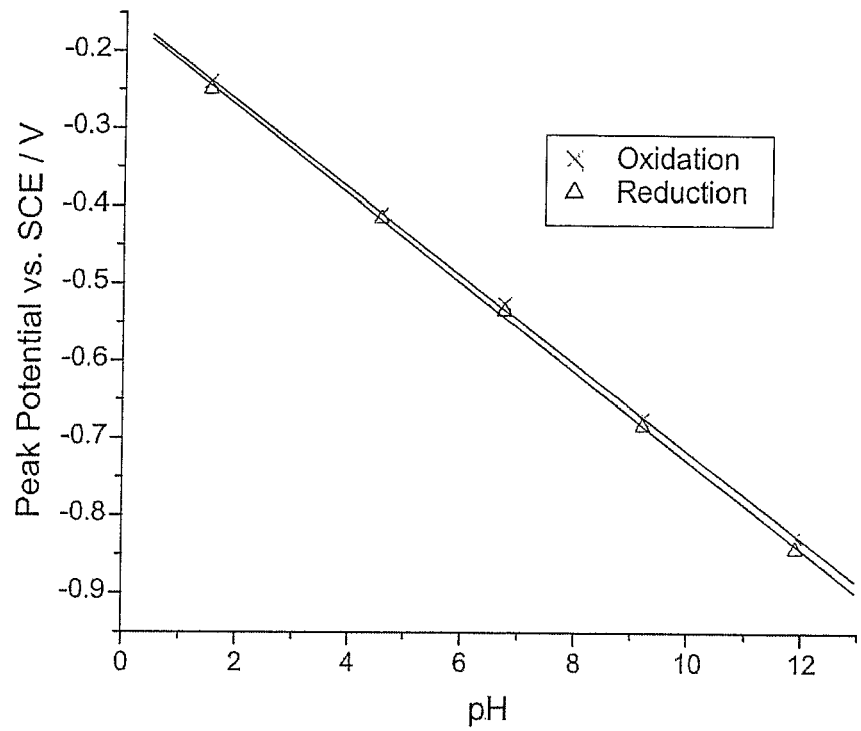
FIGS. 7B-C are plots of peak potential against pH for the redox systems of FIGS. 4C and 4D, respectively, over the pH range pH 1.0 to pH 12.0 at 293 K at various conditions.
Figure 7C:
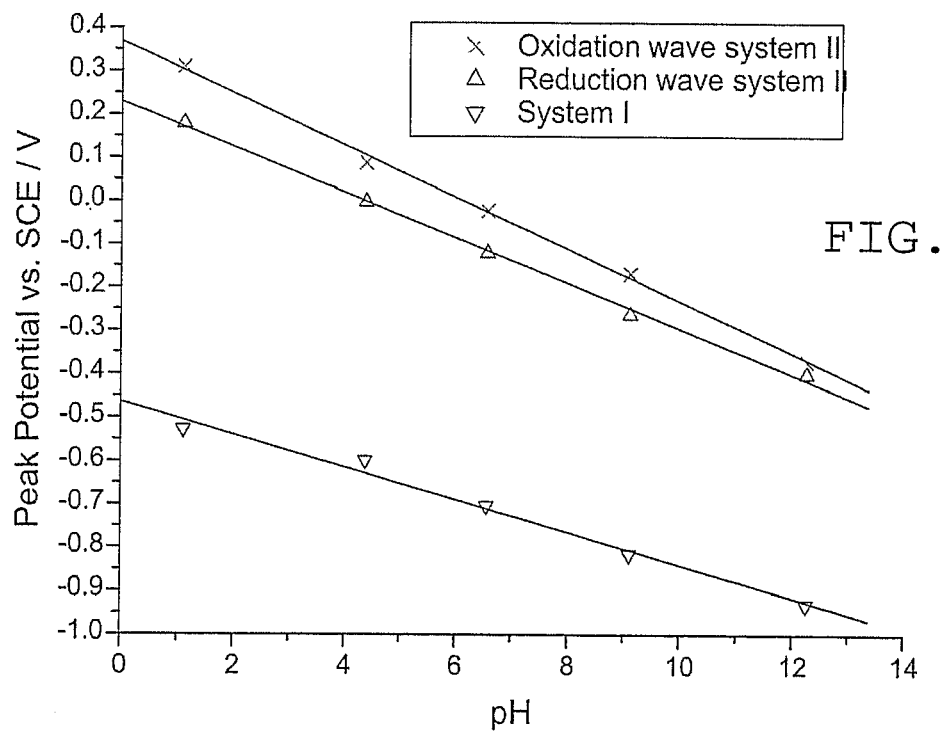

At room temperature the peak potentials for both AQ-MWCNTs and NB-MWCNTs are found to shift to more negative potentials with increasing pH as predicted. A corresponding plot of peak potential against pH was found to be linear over the entire pH range studied in all cases (see FIGS. 7B and 7C, respectively) and a comparison of the gradient of the plots of peak potential vs. pH are found to be close to the ideal value of 58.1 mV/pH unit with the exception of the irreversible peak (system I) for NB-MWCNTs which was found to shift by only 37.6 mV/pH unit.

Figure 7D:
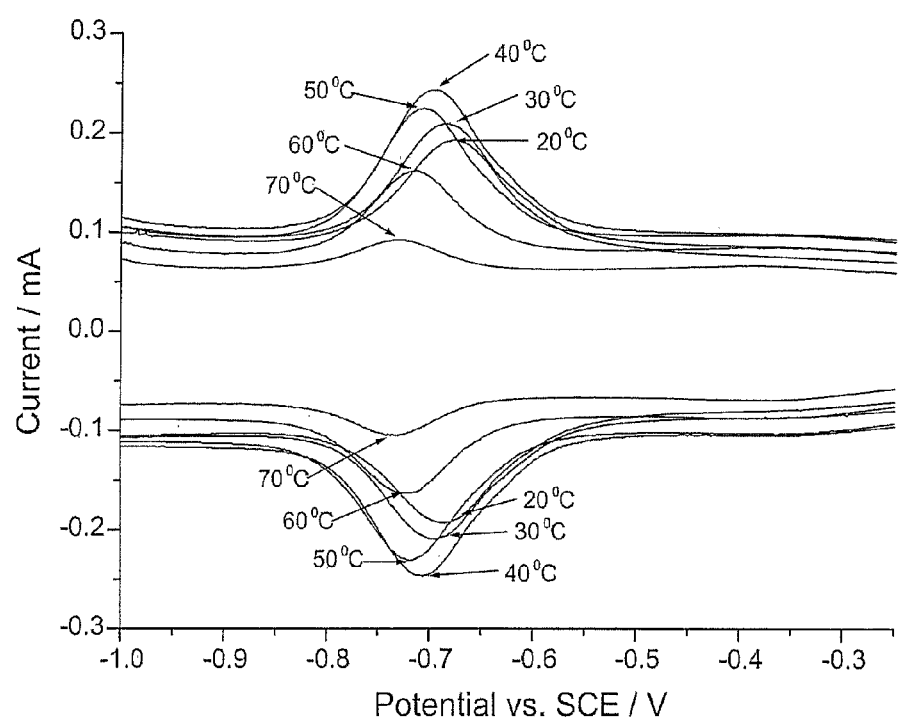
FIG. 7D illustrates that for one embodiment of the present invention when temperature is increased the peak potential is shifted to more negative values.

The response of AQ-MWCNTs to pH at elevated temperatures up to 70° C. is studied using SWV. Note that the pH of the solutions used may vary with temperature, and so to this end three IUPAC buffers with a known pH at each temperature studied were employed. These are the pH 4.6, pH 6.8 and pH 9.2 buffers. The Nernst equation predicts that the peak potential should shift to more negative values as the temperature is increased due to the temperature dependence of the formal potential ($E_{peak}^{0}$). FIG. 7D does indeed reveal that as the temperature is increased the peak potential is shifted to more negative values. However, in contrast to the behaviour of carbon powder covalently derivatised with the anthraquinonyl moiety (AQcarbon) where the peak currents increase steadily with increasing temperature after an initial increase in peak current up to ca 40° C., the peak currents for AQ-MWCNTs gradually decreases with increasing temperature. This behaviour has also been previously observed for MWCNT agglomerates at elevated temperatures. The temperature invariance of derivatised MWCNTs is not fully understood but has a potential advantage for pH sensors which are required for use in elevated temperature environments.

Figure 7E:
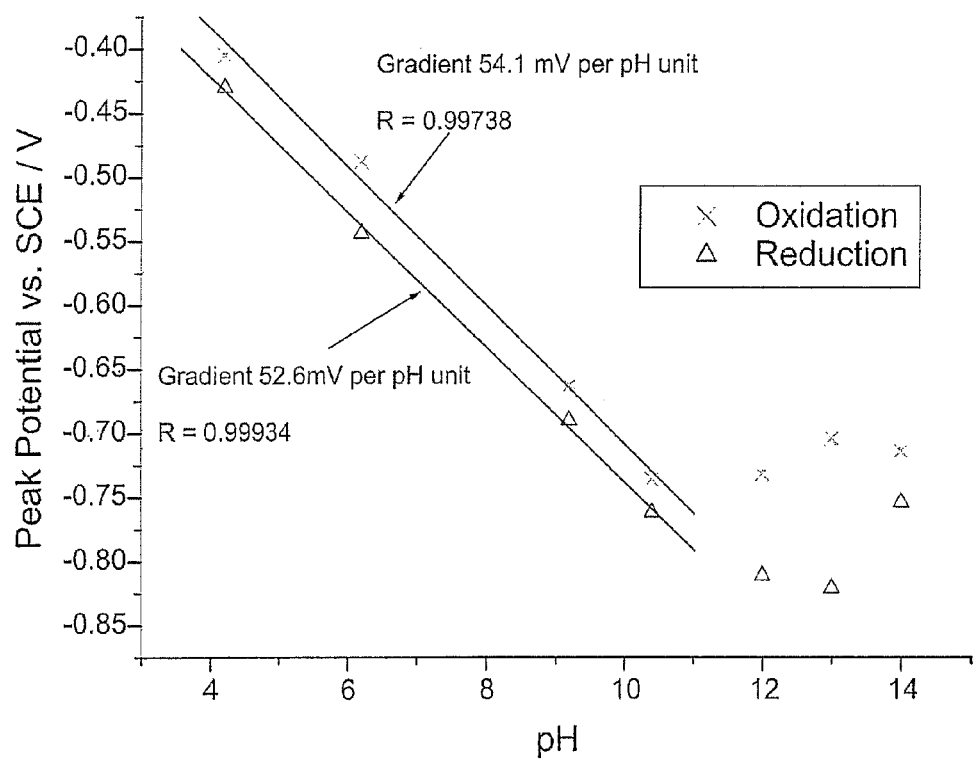
FIG. 7E illustrates the effect of varying pH at room temperature for molecular anthraquinone in the solution phase versus the AQ-MWCNTs immobilised onto a bppg electrode, in accordance with an embodiment of the present invention.

In FIG. 7E there is illustrated the effect of varying pH at room temperature for molecular anthraquinone in the solution phase versus the AQ-MWCNTs immobilised onto a bppg electrode. 1 mM anthraquinone solutions are prepared at each pH and studied using cyclic voltammetry at a bare bppg electrode. The variation of peak potential with pH for both cases over the pH range 1.0 to 14.0 are studied with additional experiments carried out at pH 10.5, pH 13.0 and pH 14.0. The plot of peak potential versus pH for both 1 mM anthraquinone in solution and for the immobilised AQ-MWCNTs reveals that, in the case of AQ-MWCNTs, a linear response is observed over the entire pH range studied. However for the anthraquinone in the solution phase, the plot is no longer linear above ca. pH 10.5 (FIG. 7E). This can be attributed to the pKa for the removal of the first proton, $pKa_1$, of the reduced form of anthraquinone (see FIG. 4C) in solution being ca. $pKa_1=10$. The pKa for the removal of the second proton is ca $pKa_2=12$. At higher pHs than pH 10 the reduced form of anthraquinone may be deprotonated causing a change in the variation of peak potential with pH. No such deviation from linearity is observed for the AQ-MWCNTs. From this it can be concluded that derivatisation onto the surface of the MWCNTs may change the $pK_a$ of the anthraquinonyl moiety. This clearly demonstrates that derivatisation onto MWCNTs proves advantageous to the analytical sensing of pH as the pH window for use is favourably widened for derivatised AQ-MWCNTs compared to free anthraquinone in solution.

Analysis of the peak potential as a function of pH at each temperature shows good agreement between the experimental and theoretically predicted values thereby showing the mechanism can be readily used as a simple, inexpensive pH probe, which works over a wide range of temperatures.

The novel probe may be placed inside various wellbore tools and installations as described in the following examples.

In FIGS. 8-11 the sensor is shown in various possible downhole applications.

Figure 8:
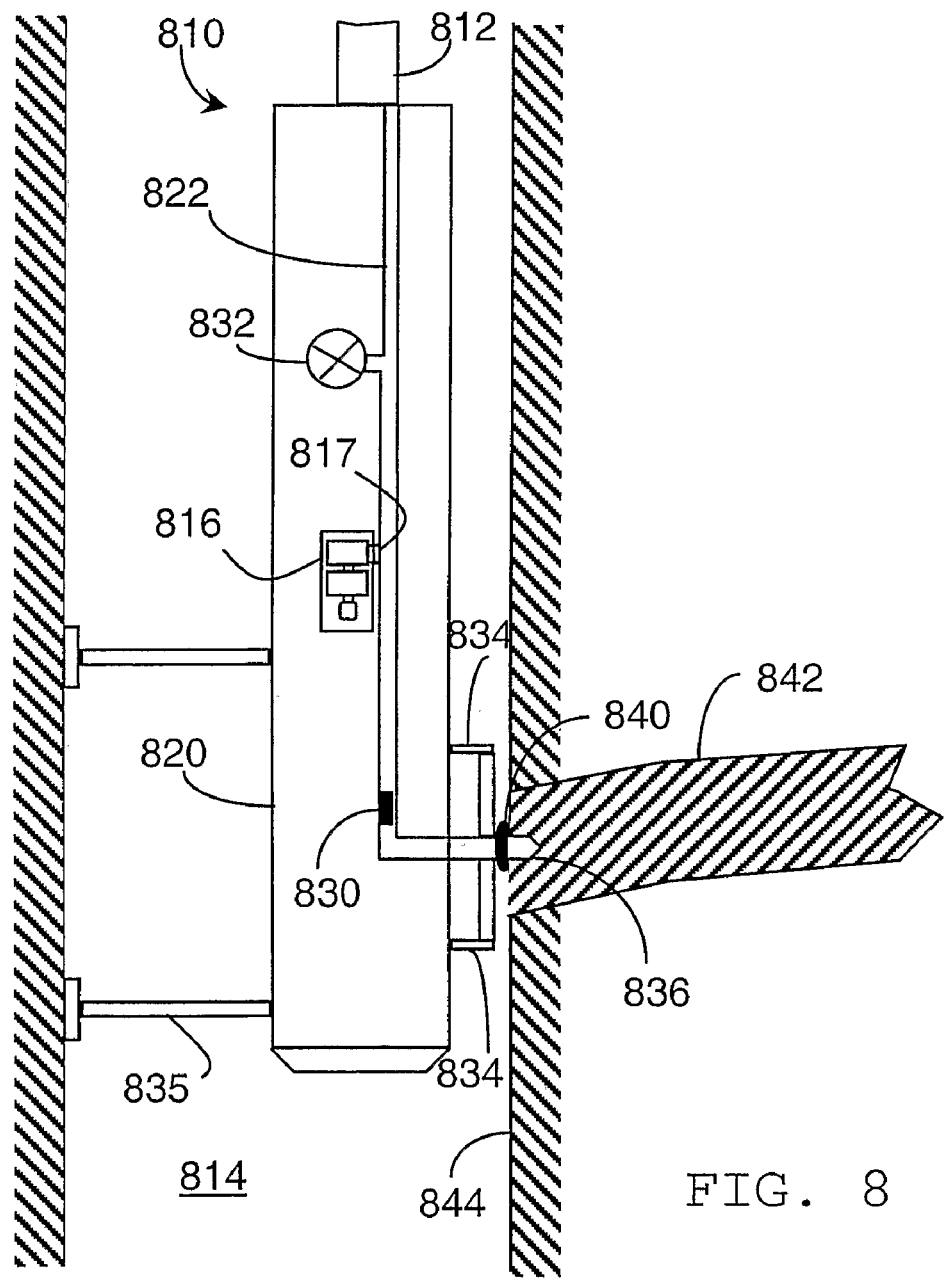
FIG. 8 illustrates an example of a sensor in accordance with the invention as part of a wireline formation testing apparatus in a wellbore.

In FIG. 8, there is shown a formation testing apparatus 810 held on a wireline 812 within a wellbore 814. The apparatus 810 is a well-known modular dynamic tester (MDT, Mark of Schlumberger) as described in the co-owned U.S. Pat. No. 3,859,851 to Urbanosky U.S. Pat. No. 3,780,575 to Urbanosky and U.S. Pat. No. 4,994,671 to Safinya et al., with this known tester being modified by introduction of a electrochemical analyzing sensor 816 as described in detail above (FIG. 8). The modular dynamics tester comprises body 820 approximately 30 m long and containing a main flowline bus or conduit 822. The analysing tool 816 communicates with the flowline 822 via opening 817. In addition to the novel sensor system 816, the testing apparatus comprises an optical fluid analyser 830 within the lower part of the flowline 822. The flow through the flowline 822 is driven by means of a pump 832 located towards the upper end of the flowline 822. Hydraulic arms 834 and counterarms 835 are attached external to the body 820 and carry a sample probe tip 836 for sampling fluid. The base of the probing tip 836 is isolated from the wellbore 814 by an o-ring 840, or other sealing devices, e.g. packers.

Before completion of a well, the modular dynamics tester is lowered into the well on the wireline 812. After reaching a target depth, i.e., the layer 842 of the formation which is to be sampled, the hydraulic arms 834 are extended to engage the sample probe tip 836 with the formation. The o-ring 840 at the base of the sample probe 836 forms a seal between the side of the wellbore 844 and the formation 842 into which the probe 836 is inserted and prevents the sample probe 136 from acquiring fluid directly from the borehole 814.

Once the sample probe 836 is inserted into the formation 842, an electrical signal is passed down the wireline 812 from the surface so as to start the pump 832 and the sensor systems 816 and 830 to begin sampling of a sample of fluid from the formation 842. The electro-chemical detector 816 is adapted to measure the pH and ion-content of the formation effluent.

A bottle (not shown) within the MDT tool may be filled initially with a calibration solution to ensure in-situ (downhole) calibration of sensors. The MDT module may also contain a tank with a greater volume of calibration solution and/or of cleaning solution which may periodically be pumped through the sensor volume for cleaning and re-calibration purposes.

Electro-chemical probes in an MDT-type downhole tool may be used for the absolute measurements of downhole parameters which significantly differ from those measured in samples on the surface (such as pH, Eh, dissolved $H_2S$, $CO_2$). This correction of surface values are important for water chemistry model validation.

A further possible application of the novel sensor and separation system is in the field of measurement-while-drilling (MWD). The principle of MWD measurements is known and disclosed in a vast amount of literature, including for example U.S. Pat. No. 5,445,228, entitled "Method and apparatus for formation sampling during the drilling of a hydrocarbon well".

Figure 9:
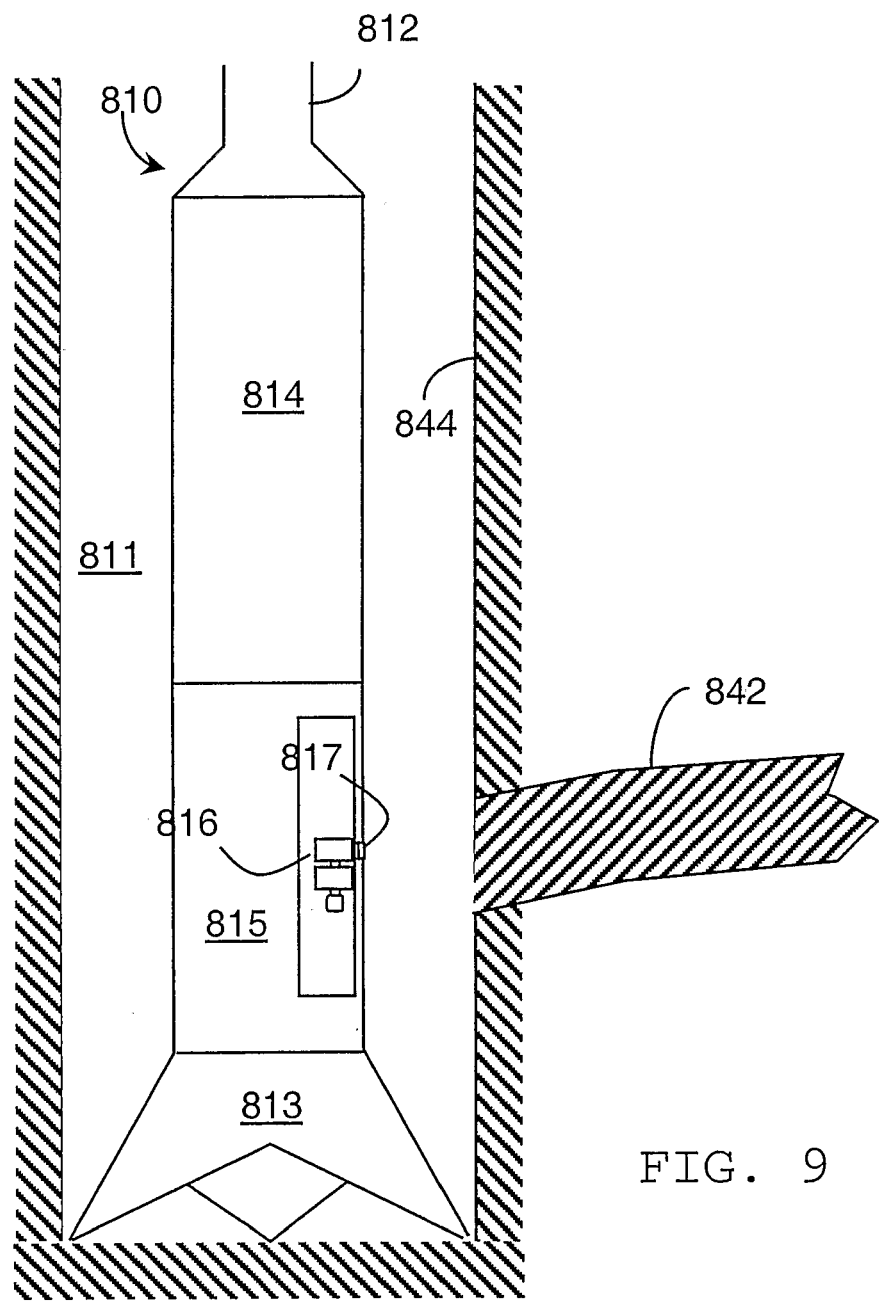
FIG. 9 shows a wellbore and the lower part of a drill string including the bottom-hole-assembly, with a sensor in accordance with the invention.

In FIG. 9, there is shown a wellbore 911 and the lower part of a drill string 912 including the bottom-hole-assembly (BHA) 910. The BHA carries at its apex the drill bit 913. It includes further drill collars that are used to mount additional equipment such as a telemetry sub 914 and a sensor sub 915. The telemetry sub provides a telemetry link to the surface, for example via mud-pulse telemetry. The sensor sub includes the novel electro-chemical analyzing unit 916 as described above. The analyzing unit 916 collects fluids from the wellbore via a small recess 917 protected from debris and other particles by a metal mesh.

During drilling operation wellbore fluid enters the recess 917 and is subsequently analyzed using sensor unit 916. The results are transmitted from the data acquisition unit to the telemetry unit 914, converted into telemetry signals and transmitted to the surface.

Figure 10:
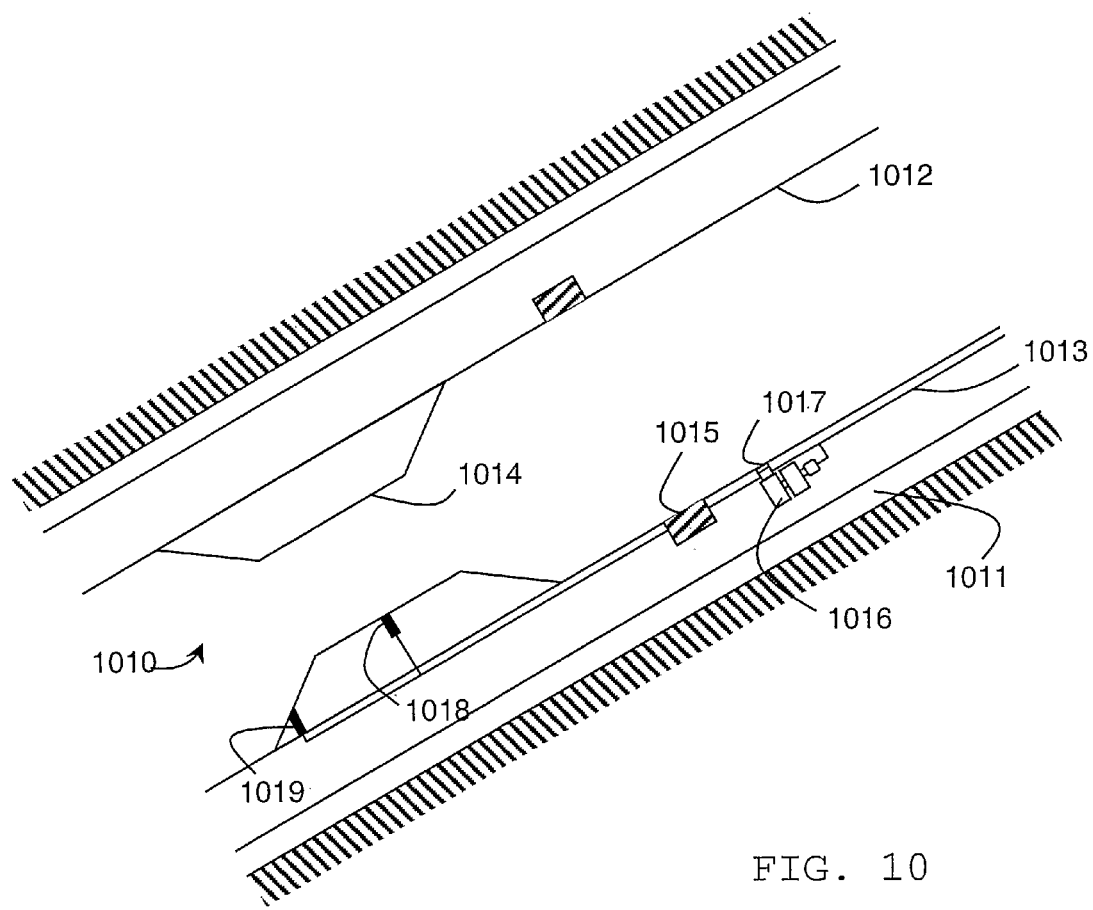
FIG. 10 shows a sensor located downstream of a venturi-type flowmeter, in accordance with the invention.

A third application is illustrated in FIG. 10. It shows a Venturi-type flowmeter 1010, as well known in the industry and described for example in the U.S. Pat. No. 5,736,650. Mounted on production tubing or casing 1012, the flowmeter is installed at a location within the well 1011 with a wired connection 1013 to the surface following known procedures as disclosed for example in the U.S. Pat. No. 5,829,520.

The flowmeter consists essentially of a constriction or throat 1014 and two pressure taps 1018, 1019 located conventionally at the entrance and the position of maximum constriction, respectively. Usually the Venturi flowmeter is combined with a densiometer 1015 located further up- or downstream.

The novel electro-chemical analyzing unit 1016 is preferably located downstream from the Venturi to take advantage of the mixing effect the Venturi has on the flow. A recess 1017 protected by a metal mesh provides an inlet to the unit.

During production wellbore fluid enters the recess 1017 and is subsequently analyzed using sensor unit 1016. The results are transmitted from the data acquisition unit to the surface via wires 1013.

Various embodiments and applications of the invention have been described. The descriptions are intended to be illustrative of the present invention. It will be apparent to those skilled in the art that modifications may be made to the invention as described without departing from the scope of the claims set out below.

The invention claimed is:

1. An electro-chemical sensor comprising:
   at least a first and a second redox system, wherein the first and the second redox systems comprise different redox systems that are sensitive to the same species, and wherein the first and the second redox systems are coupled with a conductive substrate and configured to function in use as a working electrode;
   a counter electrode;
   a reference electrode
   means to apply a varying potential to the working electrode; and
   means to detect peaks in a current flowing between the working and counter electrode as the applied voltage is varied, wherein the peaks in the current flowing between the working and counter electrodes are produced by oxidation or reduction of the first and the second redox systems and wherein the first and the second redox systems produce peak current flows at different applied potentials.

2. The sensor of claim 1 wherein the first and the second redox systems are bonded with or immobilized on the conductive substrate.

3. The sensor of claim 1 wherein the conductive substrate comprises a carbon-based substrate.

4. The sensor of claim 1 wherein the conductive substrate comprises a carbon powder substrate.

5. The sensor of claim 1 wherein the conductive substrate comprises a diamond-based substrate.

6. The sensor of claim 1 wherein the conductive substrate comprises a multi-walled nanotube-based substrate.

7. The sensor of claim 1 further comprising:
   a detector adapted to measure a redox potential of said first and said second redox system in the presence of the species and to convert measurements into an signal indicative of the concentration of said species.

8. The sensor of claim 1 wherein one of the first and second redox systems comprises one of an anthraquinone, a phenanthrenequinone and N,N'-diphenyl-p-phenylenediamine.

9. The sensor of claim 1 wherein the first and second redox systems are sensitive to H+.

10. A downhole tool for measuring characteristic parameters of wellbore effluents comprising an electro-chemical sensor in accordance with claim 1.

11. A downhole formation sampling tool for measuring characteristic parameters of wellbore effluents comprising an electro-chemical sensor in accordance with claim 1.

12. A downhole tool for measuring characteristic parameters of wellbore effluents comprising an electro-chemical sensor in accordance with claim 1 mounted onto a permanently installed part of the wellbore.

* * * * *